(12) United States Patent
Placzek et al.

(10) Patent No.: US 10,167,496 B2
(45) Date of Patent: Jan. 1, 2019

(54) SUMOYLATION ASSAY AND RELATED REAGENTS

(71) Applicant: The UAB Research Foundation, Birmingham, AL (US)

(72) Inventors: William J. Placzek, Vestavia, AL (US); Mary-Ann Bjornsti, Birmingham, AL (US); Christine M. Wright, Hoover, AL (US); Robert H. Whitaker, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 45 days.

(21) Appl. No.: 15/283,682

(22) Filed: Oct. 3, 2016

(65) Prior Publication Data

US 2017/0096698 A1    Apr. 6, 2017

Related U.S. Application Data

(60) Provisional application No. 62/235,971, filed on Oct. 1, 2015.

(51) Int. Cl.
*C12Q 1/25* (2006.01)
*C12N 9/00* (2006.01)

(52) U.S. Cl.
CPC .......... *C12Q 1/25* (2013.01); *C12N 9/93* (2013.01); *C12Y 603/02019* (2013.01); *G01N 2333/9015* (2013.01); *G01N 2440/36* (2013.01)

(58) Field of Classification Search
None
See application file for complete search history.

(56) References Cited

U.S. PATENT DOCUMENTS 8,642,256 B2    2/2014 Vogel et al.

OTHER PUBLICATIONS

Guo et al. (Biochemical Society Transactions 2007 vol. 35, p. 1414-1418 (Year: 2007).*
Wei Yang et al., "Development of a High-Throughput Screening Assay for Inhibitors of Small Ubiquitin-Like Modifier Proteases," Journal of Biomolecular Screening, 18(5), pp. 621-628, 2013.
Michael H. Tatham et al., "FRET-Based In Vitro Assays for the Analysis of SUMO Protease Activities," Methods in Molecular Biology: SUMO Protocols, vol. 497, Feb. 2009, pp. 253-268.

* cited by examiner

*Primary Examiner* — Changhwa J Cheu
(74) *Attorney, Agent, or Firm* — Kilpatrick Townsend & Stockton, LLP

(57) ABSTRACT

Provided herein and methods and kits for identifying inhibitors of SUMOylation. The provided methods include contacting a candidate agent with (i) a SUMO-conjugating peptide comprising an N-terminal linker and a detectable tag, and (ii) a SUMO comprising a metal complex, under conditions that allow binding between the SUMO-conjugating peptide and the SUMO, and detecting the detectable tag thereby determining the level of binding between the SUMO-conjugating peptide and SUMO. A reduced level of binding as compared to the level of binding in the absence of the candidate agent indicating the agent inhibits SUMOylation.

9 Claims, No Drawings
Specification includes a Sequence Listing.

SUMOYLATION ASSAY AND RELATED REAGENTS

CROSS-REFERENCES TO RELATED APPLICATIONS

This application claims priority to U.S. Provisional Application No. 62/235,971, filed Oct. 1, 2015, which is incorporated by reference herein in its entirety.

BACKGROUND

Small Ubiquitin-Like Modifier (SUMO) is a protein that is post-translationally conjugated to target proteins to alter their function, cellular location, and stability. In yeast there is one SUMO protein (Smt3), while in humans there are four SUMO homologs (SUMO-1, SUMO-2, SUMO-3, and SUMO-4). SUMO conjugation involves the initial activation of one of the SUMO homologs by proteolytic cleavage of C-terminal amino acid residues to reveal the mature Gly-Gly terminus, which is then adenylated, loaded onto the SUMO E1 enzyme, and transferred to the SUMO E2 enzyme. SUMO E2 (also known as Ubc9) is able to directly conjugate SUMO to target proteins alone, or in concert with SUMO E3 chaperones that facilitate SUMO E2 interaction with the target proteins. SUMOylation (conjugation of SUMO to a target protein) is a critical cellular process that impacts nuclear-cytosolic transport, transcriptional regulation, apoptosis, protein stability, response to stress, and progression through the cell cycle.

BRIEF SUMMARY

Provided herein are methods and kits for identifying inhibitors of SUMOylation. The provided methods include contacting a candidate agent with (i) a SUMO-conjugating peptide comprising an N-terminal linker and a detectable tag and (ii) a SUMO comprising a metal complex, under conditions that allow binding between the SUMO-conjugating peptide and the SUMO, and detecting the detectable tag to determine the level of binding between the SUMO-conjugating peptide and SUMO. A reduced level of binding as compared to the level of binding in the absence of the candidate agent indicating the agent inhibits SUMOylation. An enhanced level of binding as compared to the level of binding in the absence of the candidate agent indicating the agent enhances SUMOylation.

DETAILED DESCRIPTION

Provided herein are methods and kits for assessing conjugation of the ubiquitin-like protein, SUMO, to a target peptide. The methods utilize (a) a SUMO-conjugating peptide tagged with either (i) a fluorescent epitope (e.g., Cy-5) or (ii) a capture tag (e.g., biotin) capable of binding to a fluorescently labeled-molecule (e.g., streptavidin) and (b) a SUMO protein (e.g., Smt3, SUMO-1, SUMO-2, SUMO-3, or SUMO-4) comprising a metal complex. By way of example, when the biotin-tagged peptide is conjugated to Eu-SUMO (SUMO tagged with Europium), addition of fluorescently labeled-streptavidin (e.g., fluorescein-streptavidin) results in a signal for visualization in a Time-Resolved Fluorescence Resonance Energy Transfer (TR-FRET) between the fluorescein and europium.

Known TR-FRET assays observe the in vitro conjugation of SUMO through an antibody-conjugated metal epitope that binds SUMO (see, e.g., U.S. Pat. No. 8,642,256). Such assays provide poor sensitivity. In contrast, the present assay effectively identifies inhibitors of the SUMO conjugation reaction and can be used to quantify the effects of point mutants in one or more SUMO conjugation enzymes on SUMO conjugation. Further, the present assay reduces the components required to perform TR-FRET to a 2 or 3 component assay including (1) metal complex conjugated to a SUMO, (2) a SUMO-conjugating peptide with a detectable tag, and (3) optionally an anti-tag that binds to the detectable tag. The detectable tag can be a fluorescent molecule, e.g., fluorescein, or biotin. In the case of biotin, the anti-tag can, optionally, be avidin or streptavidin. Other known high affinity binding pairs can be used as the indirectly detectable tag and the anti-tag.

Inhibitors of SUMOylation are useful in the treatment of proliferative disorders (e.g., cancer) and the present assay is useful in the identification of inhibitors of the SUMOylation reaction. Such inhibitors optionally affect one or more steps in the reaction (e.g., adenylation of SUMO by the E1 enzyme, formation of a thiol-ester bond between SUMO and the E1 active site cysteine, transfer of SUMO to the E2 enzyme active site cysteine, and conjugation of the SUMO to the target peptide). The assay also is useful in the identification of allosteric changes in one or more of the E1 and E2 enzymes that modulate SUMOylation efficiency, non-covalent SUMO binding, or any protein-protein interactions between E1, E2, E3, SUMO, or peptide.

The assay includes contacting a SUMO-conjugating peptide (e.g., KEVGKTENDH (SEQ ID NO:1)) with an N-terminal linker (e.g., an Ahx linker) having a detectable tag with SUMO (e.g., SUMO-1), wherein the SUMO is conjugated to a metal (e.g., europium). The contacting step can be in the presence of an E1, E2, E3 enzyme, ATP, or any combination thereof. If necessary, the detectable label (e.g., biotin) is further contacted with the anti-tag (e.g., avidin or streptavidin). The detectable label is then detected using for example, a fluorescent reader, Western blot, or the like.

Provided herein are methods of identifying an inhibitor of SUMOylation. The methods include contacting a candidate agent with (i) a SUMO-conjugating peptide comprising an N-terminal linker and a detectable tag, and (ii) a SUMO comprising a metal complex, under conditions that allow binding between the SUMO-conjugating peptide and the SUMO, and detecting the detectable tag to determine the level of binding between the SUMO-conjugating peptide and SUMO. A reduced level of binding as compared to the level of binding in the absence of the candidate agent indicates the agent inhibits SUMOylation. Optionally, the detectable tag is a fluorescent molecule. Optionally, the detectable tag is biotin. Optionally, the detection comprises adding streptavidin labeled with a fluorescent molecule. Optionally, the contacting further comprises a SUMO-conjugating enzyme. Optionally, the SUMO-conjugating enzyme is selected from the group consisting of an E1 enzyme, an E2 enzyme, an E3 enzyme, or any combination thereof. Optionally, the metal complex is a metal chelate or a metal cryptate. Optionally, the metal is a lanthanide metal. Optionally, the lanthanide metal is europium or terbium. The provided methods can be used to identify inhibitors of any step in the SUMOylation pathway, for example, adenylation of SUMO by an E1 enzyme, formation of a thiol-ester bond between SUMO and an E1 enzyme active site, transfer of SUMO to an E2 enzyme active site, conjugation of SUMO to the SUMO-conjugating peptide, or any combination thereof.

As used herein, the term "SUMOylation" refers to the process of attaching and detaching endogenous one or more SUMO proteins to and from target proteins in cells to modify the function of those targeted proteins. Specifically, SUMOylation involves SUMO isoforms being conjugated to lysine residues found within a sequence in a target protein. SUMOylation requires multiple steps that are catalyzed by three types of SUMOylation enzymes: activating enzyme E1 (made up of two subunits, SAE1 and SAE2/Uba2); conjugating enzyme E2 (Ubc9); and one of several E3 ligases. SUMO is activated by the E1 enzyme through ATP hydrolysis to form a thioester conjugate with E1. SUMO is then transferred to E2, forming a thioester conjugate with E2. SUMO is then transferred to a target protein, a step usually stimulated by an E3 ligase. Inhibitors of sumoylation can inhibit any of the steps of the SUMOylation pathway.

As used herein, an inhibitor of SUMOylation or a SUMOylation inhibitor or SUMO inhibitor refers to any inhibitor that inhibits directly or indirectly the addition of a SUMO protein to a target protein. The inhibitor can be, for example, a small molecule, nucleic acid, polypeptide, or antibody (or fragment thereof).

The term candidate agent as used herein refers to any molecule to be tested in the provided methods to determine whether the candidate agent inhibits any step of the SUMOylation pathway. Candidate agents include small molecules or biomolecules. Small molecule candidate agents encompass numerous chemical classes, though typically they are organic molecules. Biomolecule candidate agents include, but are not limited to, peptides/proteins, saccharides, fatty acids, steroids, purines, pyrimidines, or antibodies (or fragments thereof) or derivatives, structural analogs or combinations thereof.

As used herein, SUMO refers to ubiquitin like proteins, including but not limited to, NEDD8, SUMO-1, UCHL3, SUMO-2, SUMO-3, SUMO4, ISG15a, ISG15b, FAT10a, FAT10b, FUB1, UBL5, URM1; ATG8; Rub1; Smt3; Hub1; Urm1; and ATG12. The term SUMO encompasses fluorescent protein—(e.g., GFP—)fusions of any of these proteins or active fragments thereof. All of these ubiquitin like polypeptides, proteins or fragments thereof can be used in the provided methods. The sequence of SUMO peptides SUMO-1, SUMO-2, and SUMO-3 is found at GenBank Accession No. NP-003343, NP-001005849, and NP-008867, respectively.

As used herein, an E1 enzyme refers to a SUMO-activating enzyme (E1) that starts the SUMOylation process. The E1 enzyme along with ATP binds to SUMO and then passes the SUMO to a SUMO carrier or conjugation protein (E2). E1 enzymes are known and include, but are not limited to, UBA1 (NG_000652 and NM_057962), UBA2 (NM_005499), UBE1C (NM_057205 and NM_003968), UBE1D1c (UBA5) (NM_001320210.1 and NP_001307139.1), UBA6 (UBE1L2) (NM_018227.5 and NP_060697.4), UBA7 (UBE1L) (NM_003335), ATG7 (GSA7) (NM_001136031.2 and NP_001129503.2), NAE1 (APPBP1) (NM_003905), and SAE1 (NM_005500 and XM_009036). Variants and fragments of E1 having SUMO-activating activity can also be used.

As used herein, an E2 enzyme refers to a SUMO-conjugating enzyme (E2) that covalently attaches SUMO to a target protein. E2 enzymes are known and include, but are not limited to, Ubc9 (P63279.1), Ubc5 (Ubch5 or Ubch5c), Ubc3 (Ubch3), Ubc4 (Ubch4) and UbcX (libel° or Ubch10), E2 ubiquitin-conjugating enzyme R1 (P49427), UbcH2 (CAA82525), UBE2D3 (NP003331), UBE2D2 (NP003330), UBE2D1 (NP003329), and UBE2C (NP008950). It is understood that many different E2 proteins are known and may be used in the provided methods as long as the E2 enzyme has SUMO-conjugating activity. Variants and fragments of E2 having SUMO-conjugating activity can also be used.

As used herein, an E3 enzyme refers to a SUMO-ligase or chaperone that assists or directly catalyzes the transfer of SUMO from an E2 enzyme to a target protein. E3 enzymes interact with both the E2 enzyme and the target protein. Many E3 ligases are known. Humans have an estimated 500-1000 E3 ligases, which impart substrate specificity onto the E1 and E2 enzymes. E3 ligases can be classified into four families, HECT, RING-finger, U-box, and PHD-finger. Thus, as used herein an E3 enzyme refers to a SUMO ligating agent comprising one or more subunits, preferably polypeptides, associated with the activity of E3 as a SUMO ligating agent (i.e., associated with the ligation or attachment of SUMO moiety to a target protein, and in some cases, to itself or another E3). Optionally, the E3 enzyme is a member of the HECT domain E3 ligating agents. Optionally, the E3 enzyme is a member of the RING finger domain E3 ligating agents. Optionally, the E3 enzyme comprises a ring finger subunit and a Cullin subunit. Examples of RING finger polypeptides s include, but are not limited to, ROC1, ROC2 and APC11. Examples of Cullin polypeptides include, but are not limited to, CUL1, CUL2, CUL3, CUL4A, CUL4B, CUL5 and APC2. Optionally, the E3 enzyme is Cst9, Mms21, Siz1 and Siz2. Optionally, the E3 enzyme is selected from the group consisting of APC, mdm2, HECTD1, HECTD2, HECTD3, PIAS1, PIAS2, PIAS3, PIAS4, RANBP2, Rbx1, Cul1, Skp1, and any combination thereof. Variants and fragments of E3 having SUMO-ligase activity can also be used.

As used herein, the term detectable tag or detectable label for use in the provided methods is meant a molecule that can be directly (i.e., a primary label) or indirectly (i.e., a secondary label) detected. For example a label can be visualized and/or measured or otherwise identified so that its presence or absence can be known. As will be appreciated by those in the art, the manner in which this is performed will depend on the label. A detectable tag includes a composition detectable by spectroscopic, photochemical, biochemical, immunochemical, chemical, or other physical means.

By fluorescent label is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 and Oregon green. Suitable optical dyes are described in the 1996 Molecular Probes Handbook by Richard P. Haugland, hereby expressly incorporated by reference. Suitable fluorescent labels also include, but are not limited to, green fluorescent protein (GFP; Chalfie, et al., Science 263(5148): 802-805 (Feb. 11, 1994); and EGFP; Clontech—Genbank Accession Number U55762), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462-471 (1998); 3. Heim, R. and Tsien, R. Y. Curr. Biol. 6:178-182 (1996)), enhanced yellow fluorescent protein (EYFP; 1. Clontech Laboratories, Inc., 1020 East Meadow Circle, Palo Alto, Calif. 94303), luciferase (Ichiki, et al., J. Immunol. 150(12): 5408-5417 (1993)), β-galactosidase (Nolan, et al., Proc Natl Acad Sci USA 85(8):2603-2607 (April 1988)) and Renilla WO 92/15673; WO 95/07463; WO 98/14605; WO 98/26277; WO 99/49019; U.S. Pat. Nos. 5,292,658; 5,418, 155; 5,683,888; 5,741,668; 5,777,079; 5,804,387; 5,874, 304; 5,876,995; and 5,925,558). All of the above-cited references are expressly incorporated herein by reference.

Labels may be indirectly detected, that is, the tag is a partner of a binding pair. By partner of a binding pair is meant one of a first and a second moiety, wherein said first and said second moiety have a specific binding affinity for each other. Suitable binding pairs for use in the invention include, but are not limited to, antigens/antibodies (for example, digoxigenin/anti-digoxigenin, dinitrophenyl (DNP)/anti-DNP, dansyl-X-anti-dansyl, fluorescein/anti-fluorescein, Lucifer yellow/anti-Lucifer yellow, and rhodamine/anti-rhodamine), biotin/avidin (or biotin/streptavidin) and calmodulin binding protein (CBP)/calmodulin. Other suitable binding pairs include polypeptides such as the FLAG-peptide (Hopp et al., BioTechnology, 6:1204-1210 (1988)); the KT3 epitope peptide (Martin et al., Science, 255:192-194 (1992)); tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87:6393-6397 (1990)) and the antibodies each thereto.

As used herein, the term metal complex refers to a metal complex that can act as a donor fluorophore in a RET or TR-RET assay. The described metal complexes are useful in the present methods because its excited state lifetime is typically on the order of milliseconds or hundreds of microseconds rather than nanoseconds; a long excited state lifetime allows detection of a molecular interaction between binding partners to be monitored after the decay of background fluorescence and/or interference from light-scattering. If a metal ion is coordinated to a chelating moiety, the complex is referred to as a metal chelate. If a metal ion is coordinated to a cryptand moiety, the complex is referred to as a metal cryptand or metal cryptate. Metals suitable for use in the provided methods include, lanthanide metals. A lanthanide metal ion can be selected from the group consisting of Sm (III), Ru (III), Eu (III), Gd (III), Tb (III), and Dy (III). Optionally, the lanthanide metal ion is europium (Eu) or terbium (Tb).

As used herein, the terms reduce, reduction, or reduced refers to a decrease in the level of expression, an activity, response, condition, disease, or other biological parameter. This includes, but is not limited to, the complete ablation of the expression, activity, response, condition, or disease. This may also include, for example, a 1% reduction in expression, activity, response, condition, or disease as compared to the native or control level. Thus, the reduction can be a 1, 5, 10, 20, 30, 40, 50, 60, 70, 80, 90, 100%, or any amount of reduction in between as compared to native or control levels.

A control or standard control refers to a sample, measurement, or value that serves as a reference, usually a known reference, for comparison to a test sample, measurement, or value. For example, in the provided methods a control can be measuring the level of binding between the SUMO and SUMO-conjugating peptide in the absence of a candidate agent or in the presence of a control agent (e.g., water). One of skill will recognize that standard controls can be designed for assessment of any number of parameters. One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

Also provided herein are kits for carrying out the provided methods. The kits include a SUMO-conjugating peptide with an N-terminal linker comprising a detectable tag and a SUMO comprising a metal complex. Optionally, the SUMO-conjugating peptide with an N-terminal linker comprising a detectable tag and the SUMO comprising a metal complex are in separate containers. Optionally, the kit includes a SUMO-conjugating peptide, an N-terminal linker, a detectable tag, a SUMO, and a metal complex, in separate containers to be prepared according to provider instructions. Optionally, the kit includes a SUMO-conjugating peptide with an N-terminal linker, a detectable tag, a SUMO and a metal complex in separate containers. Optionally, the N-terminal linker is an Ahx linker. Optionally, the detectable tag is a fluorescent molecule. Optionally, the metal complex is a metal chelate or a metal cryptate. Optionally, the metal is a lanthanide metal. Optionally, the lanthanide metal is europium or terbium. Optionally, the kit further comprises a SUMO-conjugating enzyme. Optionally, the SUMO-conjugating enzyme is selected from one or more of the group consisting of an E1 enzyme, an E2 enzyme, and an E3 enzyme. Optionally, the detectable tag is biotin and the kit further comprises avidin or streptavidin labeled with a fluorescent molecule. Optionally, the kit further comprises one or more buffers, reagents, or devices for detecting the detectable label. Thus, the kit can further include assay containers (tubes, plates, or the like), buffers, or enzymes necessary for carrying out the provided methods.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

A number of embodiments have been described. Nevertheless, it will be understood that various modifications may be made. Accordingly, other embodiments are within the scope of the claims.

EXAMPLES

Example 1

TR-FRET Assay

A SUMO-conjugating peptide, e.g., KEVGKTENDH (SEQ ID NO:1) is synthesized with an N-terminal linker such as Ahx. A detectable tag such as fluorescein or biotin is attached to the Ahx-SUMO-conjugating peptide (hereafter referred to as biotin-SCP or FITC-SCP). Peptide concentration is determined using NMR spectroscopy. SUMO is recombinantly expressed and purified from bacteria. The metal complex is conjugated to SUMO and stored at −80 degrees. SUMO E1 and SUMO E2 are thawed on ice. A reaction solution is made containing E1, Eu-SUMO1, E2, and Biotin-SCP at a concentration of 1.6 µM, 10.9 µM, 4 µM, or 160 µM in 1× reaction buffer (5 mM Tris pH 7.6, 10 mM MgCl2, 20 mM NaCl). ATP is added to the reaction solution. The reaction solution is incubated at 37° C. for 2 hours. The reactions are diluted 1:1000 in 1× reaction buffer. Ten (10) µl of each reaction is added to a white OptiPlate-384 from Perkin Elmer or comparable plate. Ten (10) µl of U-light Streptavidin master mix is added to each well (master mix contains 16 nM Ulight streptavidin in detection buffer (50 mM Tris pH=7.5, 0.1% BSA)). The reactions are incubated at room temperature for 1 hour. The reactions are read on VICTOR™ (PerkinElmer, Waltham, Mass.) or comparable plate reader.

Example 2

Gel Analysis of SUMO Conjugation

The SUMOylation reaction is performed as outlined in Example 1. SDS loading buffer is added to each reaction sample at 1:3 ratio. The proteins are separated using polyacrylamide gel electrophoresis. Reactions are observed using gel imaging system capable of observing fluorescein directly in the gel if FITC-SCP is used. Alternatively, using Biotin-SCP, the proteins are transferred from the gel to a membrane (as performed for Western blot), and visualized using IRDye 680RD Streptavidin.

Example 3

Comparison with Assays Requiring Metal Conjugated Anti-GST or Anti-His Antibodies Assays requiring metal conjugated anti-GST or anti-His antibodies exhibited poor FRET transfer and signal intensity. By directly conjugating the metal to the SUMO protein, the FRET distance is decreased and the transfer efficiency and signal intensity is improved substantially. LANCE Europium ITC (PerkinElmer) can be used to make europium conjugated SUMO and LANCE Ultra Ulight-streptavidin (PerkinElmer) reagent can be used to bind to the biotin-tagged peptide.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of identifying an inhibitor of sumoylation comprising:
   (a) contacting a candidate agent with (i) a small ubiquitin-like modifier (SUMO)-conjugating peptide comprising an N-terminal linker and a detectable tag, and (ii) a SUMO comprising a metal chelate or a metal cryptate, under conditions that allow binding between the SUMO-conjugating peptide and the SUMO; and
   (b) detecting the detectable tag thereby determining the level of binding between the SUMO-conjugating peptide and SUMO;
   a reduced level of binding as compared to the level of binding in the absence of the candidate agent indicating the agent inhibits sumoylation.

2. The method of claim 1, wherein the detectable tag is a fluorescent molecule.

3. The method of claim 1, wherein the detectable tag is biotin.

4. The method of claim 3, wherein the detecting comprises adding streptavidin labeled with a fluorescent molecule.

5. The method of claim 1, wherein the contacting further comprises a SUMO-conjugating enzyme.

6. The method of claim 1, wherein the SUMO-conjugating enzyme is selected from the group consisting of an E1 enzyme, an E2 enzyme, an E3 enzyme or a combination thereof.

7. The method of claim 1, wherein the metal is a lanthanide metal.

8. The method of claim 7, wherein the lanthanide metal is europium or terbium.

9. The method of claim 1, wherein the method identifies inhibitors of adenylation of SUMO by an E1 enzyme, formation of a thiol-ester bond between SUMO and an E1 enzyme active site, transfer of SUMO to an E2 enzyme active site, conjugation of SUMO to the SUMO-conjugating peptide, or any combination thereof.

* * * * *

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial sequence
<220> FEATURE:
<223> OTHER INFORMATION: Synthetic construct

<400> SEQUENCE: 1

Lys Glu Val Gly Lys Thr Glu Asn Asp His
1               5                   10
```